United States Patent [19]

Robinson

[11] 4,043,322
[45] Aug. 23, 1977

[54] SURGICAL SCRAPING INSTRUMENT

[76] Inventor: Ralph R. Robinson, P.O. Box 668, Middlesboro, Ky. 40965

[21] Appl. No.: 686,015

[22] Filed: May 13, 1976

[51] Int. Cl.² .................. A61B 1/00; A61B 17/22; A61M 1/00
[52] U.S. Cl. .................. 128/2 B; 128/278; 128/304
[58] Field of Search ......... 128/2 B, 276, 304, 278

[56] References Cited

U.S. PATENT DOCUMENTS

| 1,080,929 | 12/1913 | Romeo | 128/304 |
| 2,715,899 | 8/1955 | MacLean | 128/304 X |
| 3,506,010 | 4/1970 | Murr | 128/276 |
| 3,721,244 | 3/1973 | Elmaleh | 128/304 |

FOREIGN PATENT DOCUMENTS

| 327,091 | 3/1903 | France | 128/304 |
| 705,401 | 3/1931 | France | 128/304 |
| 362,997 | 11/1922 | Germany | 128/304 |

Primary Examiner—Channing L. Pace
Attorney, Agent, or Firm—Schmidt, Johnson, Hovey & Williams

[57] ABSTRACT

A simplified, easy-to-use surgical scraping instrument or curette especially adapted for obtaining uterine tissue or material samples is provided which includes a suction tube having cooperable scraping loop and tissue-catching structure adjacent one end thereof for easily and safely obtaining tissue samples from the uterine wall of a patient. In preferred forms the material-receiving opening of the tube is generally elliptical in configuration and obliquely disposed adjacent an oppositely and upwardly extending scraping loop presenting a relatively sharp, continuous upper scraping edge. The outermost bight section of the scraping loop is advantageously disposed at an angle relative to the remainder of the loop in order to present an outermost arcuate scraping area.

2 Claims, 6 Drawing Figures

SURGICAL SCRAPING INSTRUMENT

This invention relates to a surgical scraping instrument or curette especially adapted for taking tissue or material samples from the walls of the uterus through the cervix opening. More particularly, it is concerned with such a scraping instrument which includes a suction tube having a specially configured, obliquely disposed scraping loop in conjunction with structure presenting material-catching means for facilitating the procedure of taking uterine wall samples.

In many medical procedures it is desirable to obtain tissue or material samples from the internal walls of the human uterus. For example, many biopsy procedures require that such samples be taken. In this connection, a number of curettes or scraping instruments have been proposed in the past for the purpose of taking uterine samples, and certain of these have achieved wide acceptance by the medical profession.

For example, see U.S. Pat. Nos. 3,491,747, 3,635,222 and 3,670,732. The present invention represents an improvement on certain types of these known curettes in order to further facilitate the taking of uterine samples in the easiest and most painless manner. However, the surgical procedures used with the present instrument are conventional and in many respects identical to those described in the above patents, and therefore reference may be had to the latter for a complete description and illustration of such procedures.

An important object of the present invention is to provide a surgical scraping instrument or curette especially adapted for the taking of uterine wall tissue or material samples and which is safe and easy to use by a practiced physician with a minimum amount of discomfort and pain to the patient.

As a corollary to the foregoing, another object of the invention is to provide a surgical scraping instrument which includes an elongated suction tube having an open, material-receiving end in conjunction with a stationary scraping loop presenting converging legs respectively connected to the tube on opposite sides of the material-receiving opening and which presents a relatively sharp scraping surface around at least a portion of the loop; in preferred forms, the loop legs are disposed in a first plane at an acute angle relative to the longitudinal axis of the tube, while the bight section of the loop is disposed to lie in a second plane at a different acute angle to the first plane and tube axis in order to present an uppermost scraping area on the loop.

A still further object of the invention is to provide a scraping instrument of the type described wherein the material-receiving opening in the end thereof is obliquely oriented and generally elliptical in configuration, with the tube structure underlying the material-receiving opening being configured to present material-catching structure cooperable with the scraping loop for catching loosened uterine material or tissue resulting from back and forth scraping movement of the instrument.

Figure 1:
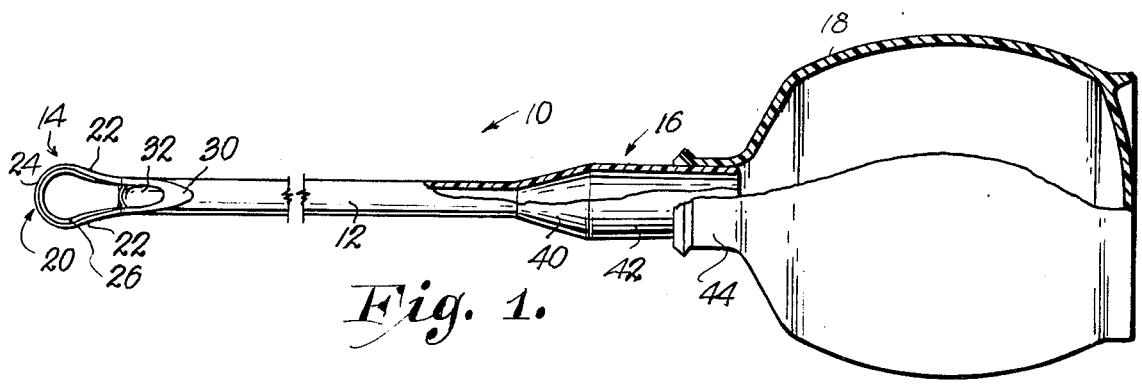
FIG. 1 is a fragmentary plan view of the scraping instrument in accordance with the invention, shown with a vacuum bulb mounted on the rearward end thereof and with parts broken away for clarity.
Figure 2:
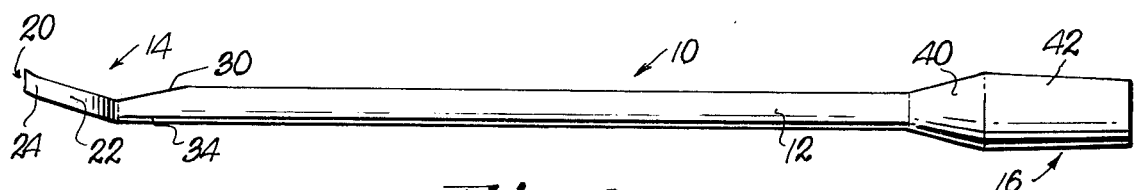
FIG. 2 is a side elevational view of the preferred scraping instrument in accordance with the invention.

Scraping instrument 10 is a unitary member formed of yieldable synthetic resin material and broadly includes an elongated suction tube 12 having a scraping end 14 and a vacuum connection end 16 adapted for connection to means such as a bulb 18 for selectively producing a negative pressure within tube 12 during uterine scraping operations.

Figure 4:
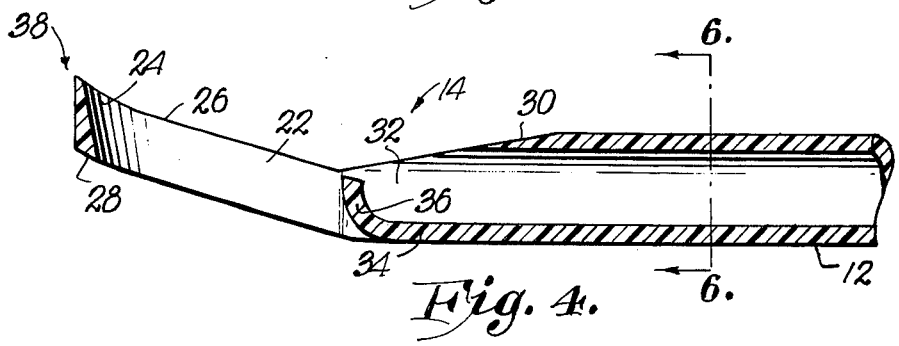
FIG. 4 is a sectional view taken along 4—4 of FIG. 3 and further illustrating the construction of the material-receiving end of the scraping instrument.
Figure 5:
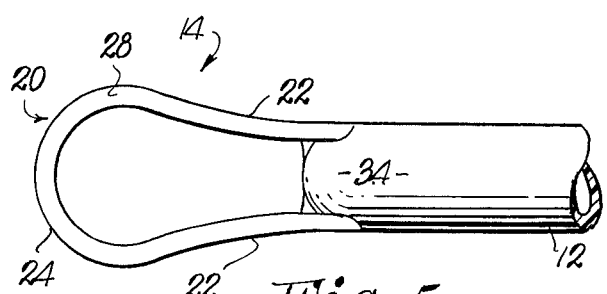
FIG. 5 is a fragmentary bottom plan view of the material-receiving end of the scraping instrument.
Figure 6:
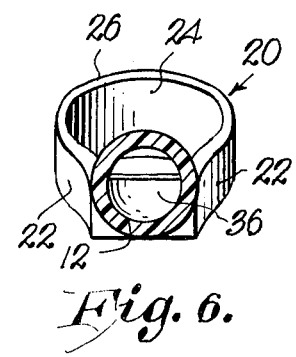
FIG. 6 is a vertical sectional view taken along lines 6—6 of FIG. 6 and further illustrating the construction of the scraping instrument hereof.

In more detail, scraping end 14 includes a unitary, stationary, vertically tapered loop 20 which presents a pair of spaced, adjacent, converging legs 22 which are respectively connected to tube 12 adjacent to the outermost end thereof. In addition, loop 20 includes an arcuate, generally semicircular bight portion 24 which interconnects legs 22 and is spaced from the adjacent end of tube 12. As best seen in FIG. 4, legs 22 and bight section 24 are cooperatively configured to present a relatively sharp scraping surface 26 around the upper periphery of loop 20. As will be seen, surface 26 is substantially uniform and continuous around the entire periphery of loop 20, while the latter has a relatively broad undersurface 28.

Figure 3:
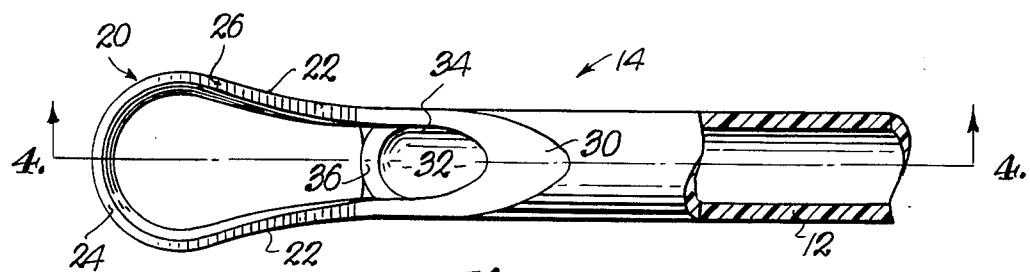
FIG. 3 is an enlarged, fragmentary plan view of the material-receiving end of the scraping instrument.

The outermost end of tube 12 is obliquely cut as at 30 relative to the longitudinal axis of tube 12 in order to present a generally elliptical material-receiving opening 32 adjacent the outermost end of the tube. Referring specifically to FIG. 4, it will be seen that the underside of tube 12 spaced from opening 32 defines a material-catching portion 34 extending towards bight section 24 and terminating in a generally upright wall portion 36 situated between loop legs 22 (see FIG. 3).

In preferred forms, loop 20 is formed in such a manner that the respective legs 22 are disposed in a first plane which is at an acute angle relative to the longitudinal axis of tube 12, while at least the outermost portion of bight section 24 is disposed in a second plane which lies at a different acute angle than the first plane and tube axis. This relative orientation of these loop-defining sections is best seen in FIG. 4, and serves to produce an uppermost scraping area generally referred to by the numeral 38. It will also be noted that oblique cut 30 in the outermost end of tube 12 is along a line which is at an obtuse angle to the above-described planes.

The rearmost end of tube 12 includes a flared, generally frustoconical section 40 and a converging, uniformly tapered extreme end 42. As best seen in FIG. 1, end 42 is especially adapted to fit within the tubular collar 44 of bulb 18. In other cases however a conventional vacuum line coupled with a vacuum pump can be used for creating the needed negative pressure within tube 12.

The use of scraping instruments or curettes is well-known to the medical profession, and need not be described in detail herein. Furthermore, such use is fully described in co-owned U.S. Pat. Nos. 3,491,747, 3,635,222 and 3,670,732, and reference should be had to these patents for details. Broadly however, in obtaining a uterine sample, end 14 of tube 12 is inserted into the cervix opening of the patient, whereupon the surgeon can manipulate tube 12 in a scraping fashion along the uterine wall. By virtue of the specialized, cooperating construction of loop 20, material-receiving opening 32 and material-catching structure 34, the surgeon can, by proper manipulation of tube 12, easily obtain a uterine sample. In this connection, the uppermost scraping area 38 of loop 20 is configured with respect to material-catching portion 34 and opening 32 therebelow for obtaining such samples with a minimum of time and discomfort to the patient. Of course, a negative pressure is created within tube 12 during the surgical procedure in order to draw the uterine tissue or material sample into the tube, and this can be done by way of manipulation of bulb 18 or through any one of a number of other conventional expedients. In any event, it will be appreciated that the specialized configuration of instrument 10 greatly facilitates taking of a wide variety of tissue samples, particularly those from the walls of a uterus.

Having thus described the invention, what is claimed as new and desired to be secured by Letters Patent is:

1. A surgical scraping instrument, comprising:
    an elongated, tubular, substantially rectilinear suction tube having a material-receiving end, with the remaining end thereof adapted for connection to means for producing a negative pressure within said tube,
    said material-receiving end being obliquely cut relative to the longitudinal axis of said tube and only partially across the diameter of the latter, for presenting an obliquely disposed planar surface having a generally elliptical, material-receiving opening therein at said material-receiving end, along with cooperable material-catching structure defined at least in part by the uncut portion of said tube adjacent and opposite to said opening, said material-catching structure also including an end wall portion at the extreme end of said uncut portion remote from said remaining end which extends towards said opening; and
    a scraping element including a unitary loop of material presenting a pair of converging legs respectively connected to the material-receiving end of said tube on opposite sides of said opening and with said end wall portion therebetween, and an arcuate bight segment in spaced relationship to said opening and interconnecting said legs,
    said spaced legs being oriented such that a majority of the lengths of the upper edges of the legs, when said tube is positioned with said opening facing upwardly, lie in a reference plane oriented at an acute angle relative to the longitudinal axis of said tube and at an obtuse angle relative to said planar surface, and with a portion of the edges of said legs being located at a first level above said opening,
    at least the central portion of said bight segment remote from said opening being oriented such that the uppermost section thereof, when said tube is positioned with said opening facing upwardly, presents a protruding portion which lies at a second level above said reference plane and opening,
    at least the edge of said bight segment contiguous with said leg edges being configured to present a scraping surface,
    said scraping surface, opening and material-catching structure being cooperatively configured and oriented for catching material loosened by movement of said scraping surface along a uterine wall or the like.

2. The surgical scraping instrument as set forth in claim 1, wherein said upper edges of said legs, and said edges of said bight segment, present a substantially uniform and continuous scraping surface around the entire periphery of said loop.

* * * * *